(12) United States Patent
Jung et al.

(10) Patent No.: US 10,894,941 B2
(45) Date of Patent: Jan. 19, 2021

(54) MICROFLUIDIC MULTI-WELL-BASED CELL CULTURE TESTING DEVICE

(71) Applicants: QUANTA MATRIX CO,. LTD., Seoul (KR); Seoul National University R&DB Foundation, Seoul (KR)

(72) Inventors: Yong Gyun Jung, Seoul (KR); Eun Geun Kim, Gunpo (KR); Sung hoon Kwon, Seoul (KR); Jung Il Choi, Seoul (KR)

(73) Assignee: QUANTAMATRIX INC., Seoul (KR)

( * ) Notice: Subject to any disclaimer, the term of this patent is extended or adjusted under 35 U.S.C. 154(b) by 678 days.

(21) Appl. No.: 14/888,530

(22) PCT Filed: May 2, 2014

(86) PCT No.: PCT/KR2014/003977
§ 371 (c)(1),
(2) Date: Nov. 2, 2015

(87) PCT Pub. No.: WO2014/178692
PCT Pub. Date: Nov. 6, 2014

(65) Prior Publication Data
US 2016/0075985 A1    Mar. 17, 2016

(30) Foreign Application Priority Data

May 2, 2013    (KR) .................. 10-2013-0049681

(51) Int. Cl.
*C12M 1/32*    (2006.01)
*C12M 3/06*    (2006.01)
(Continued)

(52) U.S. Cl.
CPC ............ *C12M 23/16* (2013.01); *C12M 21/18* (2013.01); *C12M 23/12* (2013.01); *C12M 23/22* (2013.01); *C12M 29/06* (2013.01); *C12Q 1/18* (2013.01)

(58) Field of Classification Search
CPC ............ C12M 23/12; B01L 2300/0829; B01L 2300/0818; B01L 2300/0864
See application file for complete search history.

(56) References Cited

U.S. PATENT DOCUMENTS

2002/0155515 A1    10/2002    Farina et al.
2007/0166199 A1    7/2007    Zhou et al.
(Continued)

FOREIGN PATENT DOCUMENTS

AU    722763 B2    8/2000
CN    1678729 A     10/2005
(Continued)

OTHER PUBLICATIONS

Gallo et al., "Demonstration of Bacillus cereus in Orthopaedic-Implant-Related Infection with Use of a Multi-Primer Polymerase Chain Reaction-Mass Spectrometric Assay", The Journal of Bone & Joint Surgery, vol. 93-A, No. 15, Aug. 3, 2011, pp. 1-6.
(Continued)

*Primary Examiner* — Jonathan M Hurst
(74) *Attorney, Agent, or Firm* — STIP Law Group, LLC

(57) ABSTRACT

A microfluidic multi-well-based cell culture testing device is provided. The multi-well-based cell culture testing device has an array structure of a plurality of aligned microfluidic well units. Each of the microfluidic well units comprises an inlet through which a first fluid enters, an accommodation compartment adapted to accommodate a second fluid
(Continued)

therein, a microfluidic channel through which the first fluid flows, and an air outlet adapted to facilitate the entering of the first fluid.

12 Claims, 12 Drawing Sheets

(51) Int. Cl.
*C12M 1/00* (2006.01)
*C12M 1/40* (2006.01)
*C12Q 1/18* (2006.01)

(56) References Cited

U.S. PATENT DOCUMENTS

| | | | |
|---|---|---|---|
| 2012/0003732 A1 | 1/2012 | Hung et al. | |
| 2012/0009671 A1 | 1/2012 | Hansen | |
| 2012/0328488 A1* | 12/2012 | Puntambekar | B01L 3/5025 422/503 |
| 2013/0059322 A1 | 3/2013 | Hung et al. | |

FOREIGN PATENT DOCUMENTS

| | | |
|---|---|---|
| CN | 1904620 A | 1/2007 |
| CN | 101285807 A | 10/2008 |
| CN | 101506656 A | 8/2009 |
| CN | 101541962 A | 9/2009 |
| CN | 101981455 A | 2/2011 |
| CN | 102947710 A | 2/2013 |
| JP | 2009210392 A | 9/2009 |
| KR | 1020070033685 | 7/2007 |
| WO | 2011081434 A2 | 7/2007 |
| WO | 2009024595 A2 | 2/2009 |
| WO | 2013038925 A1 | 3/2013 |

OTHER PUBLICATIONS

Anderson et al., "Intracellular Bacterial Biofilm-Like Pods in Urinary Tract Infections", www.sciencemag.org Science vol. 301, Jul. 4, 2003 pp. 105-107.
International Search Report for PCT/KR2014/003977 dated Aug. 26, 2014.
Pincus, David H., Microbial Identification Using the Biomerieux Vitek 2 System, Parenteral Drug Association, Mar. 2014, pp. 1-32, www.pda.org/bookstore, Relevant passage includes full disclosure.
Wu, Min-Hsien et al., Microfluidic cell culture systems for drug research, Lab on a Chip, The Royal Society of Chemistry, Jan. 21, 2010, 939-956, vol. 10, www.rsc.org/loc. See Abstract.

* cited by examiner

[Fig. 1]
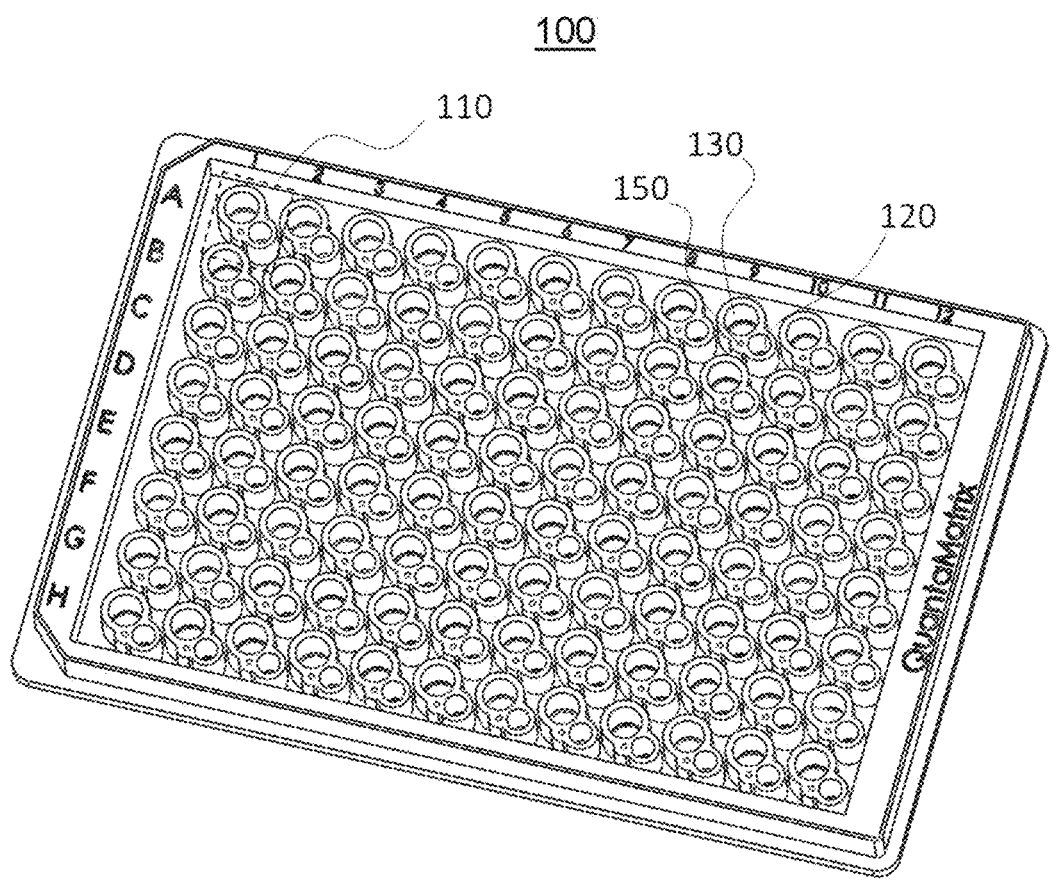

[Fig. 2]
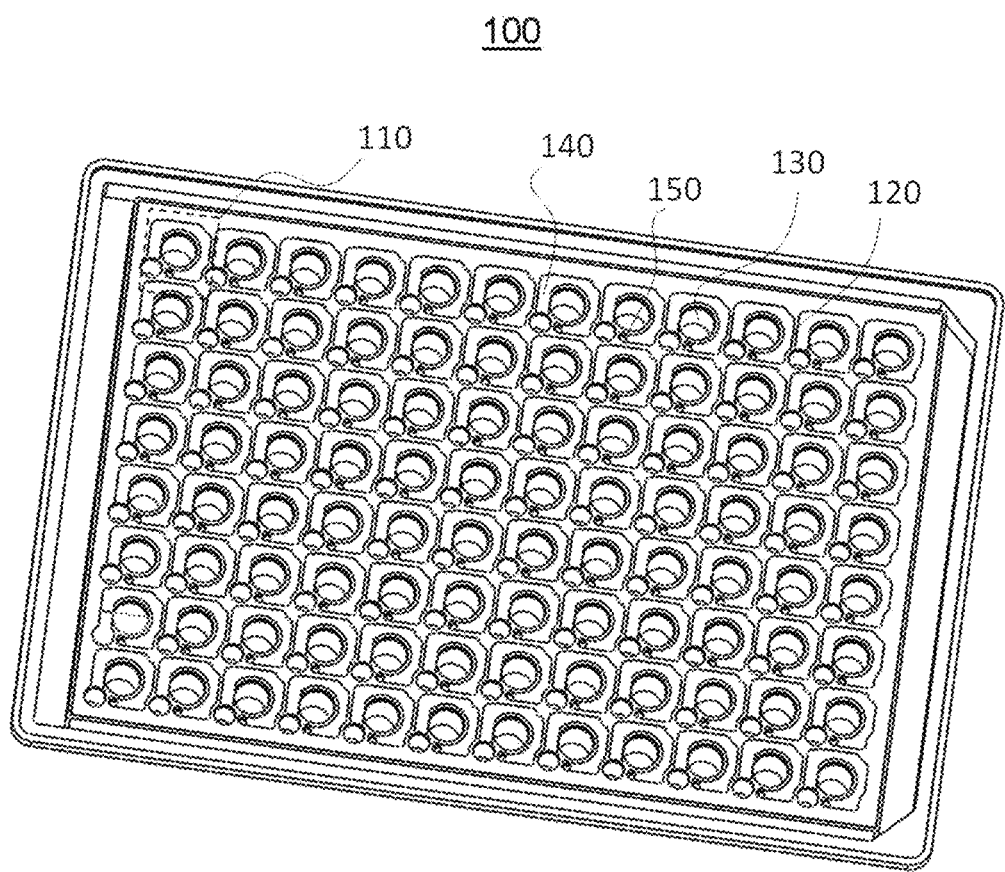

[Fig. 3]
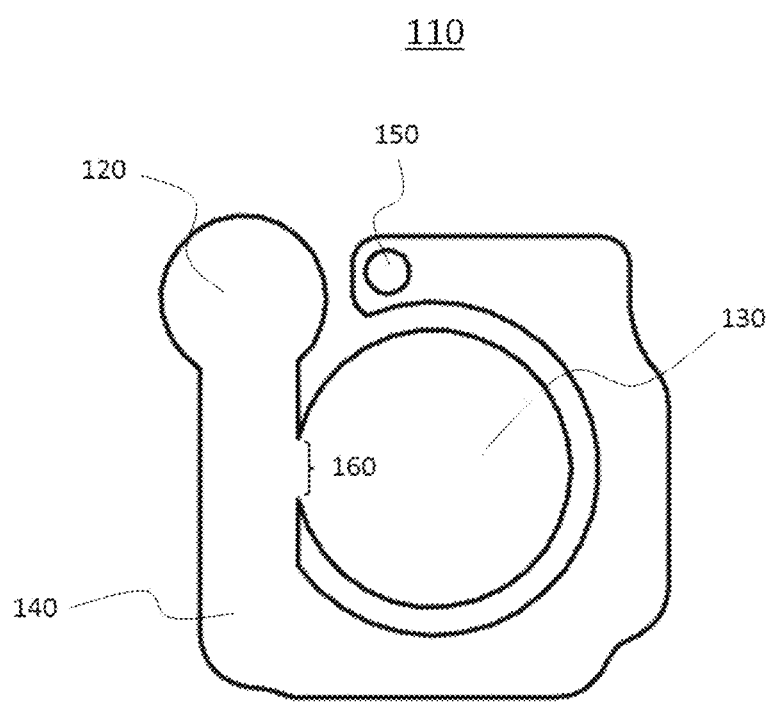

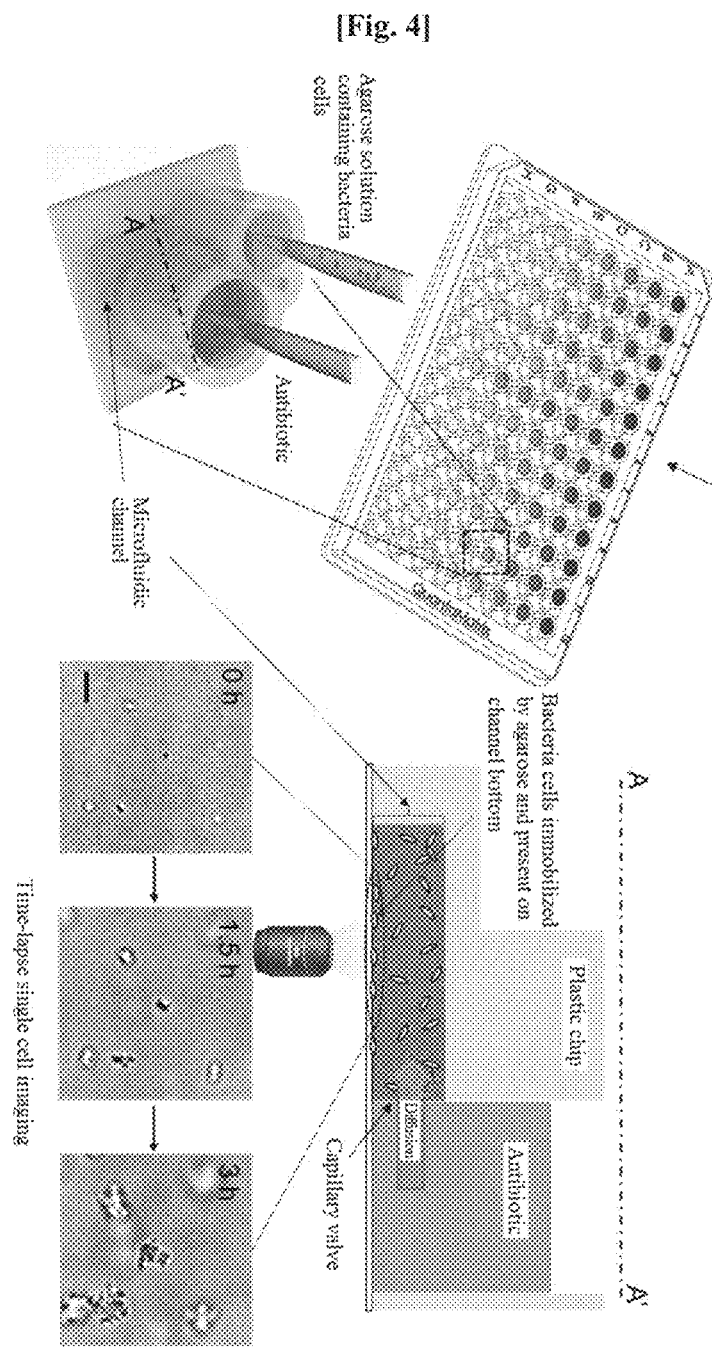
[Fig. 4]

[Fig. 5]
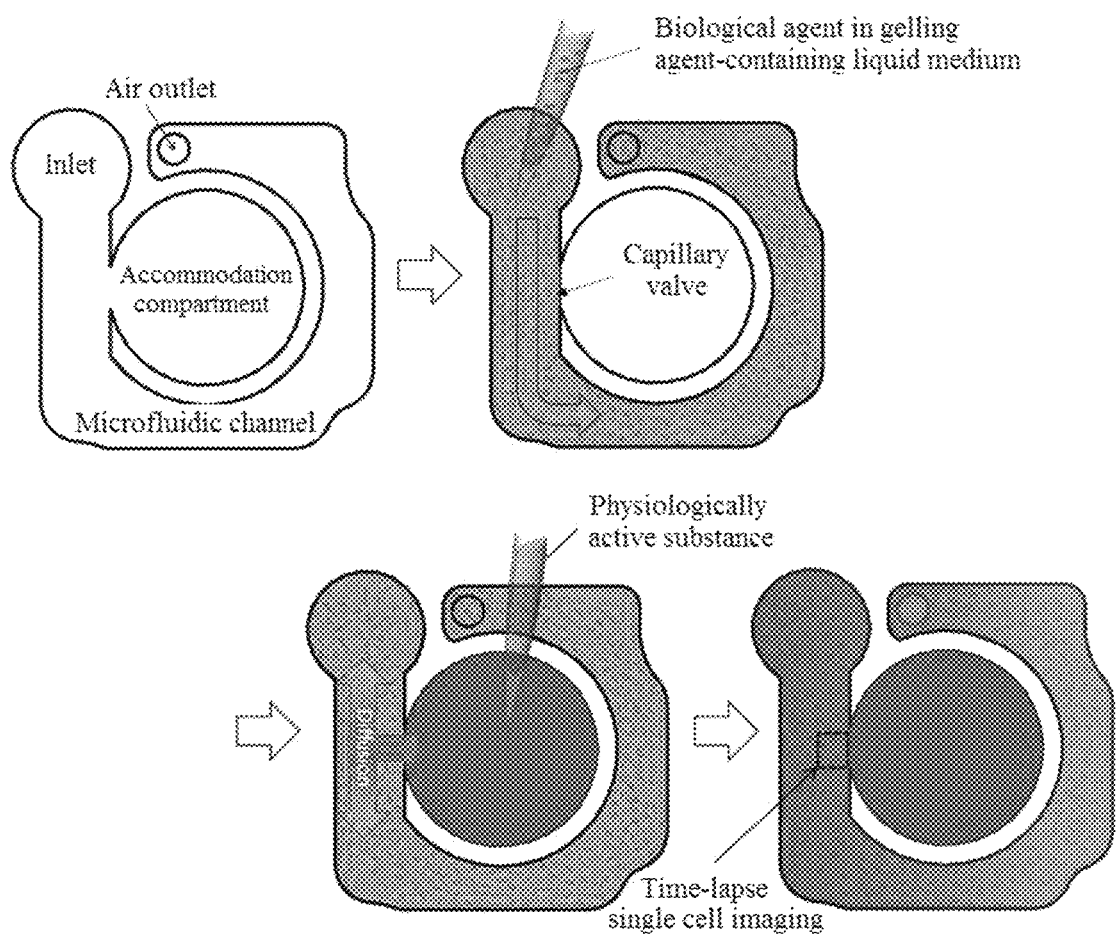

[Fig. 6]
*Strain* : *E. facalis* 1.5% , Antibiotic : penicillin (ug/ml), 4hrs incubation
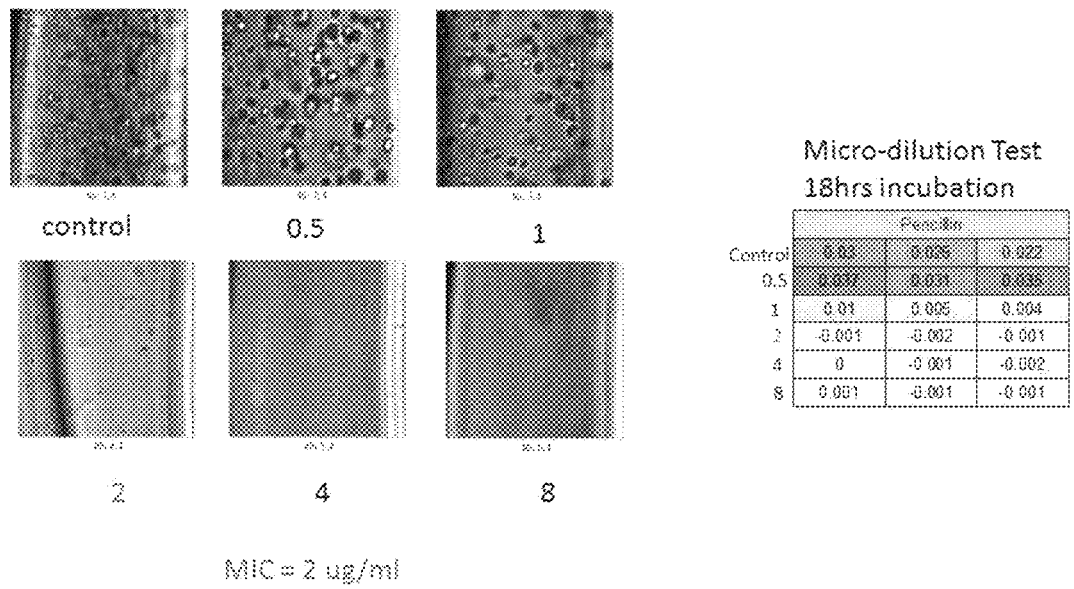
MIC = 2 ug/ml
[Fig. 7]
*Strain* : *E. coli* 1.5% , Antibiotic : Gentamicin (ug/ml), 4hrs incubation
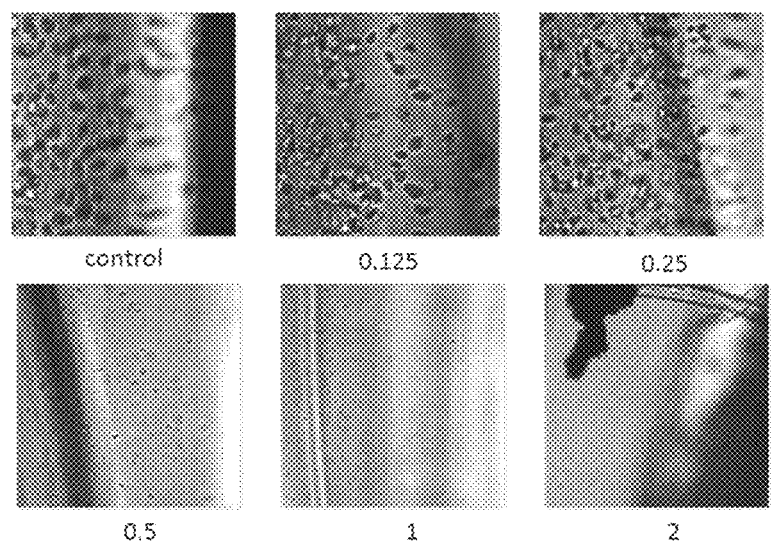

[Fig. 8]
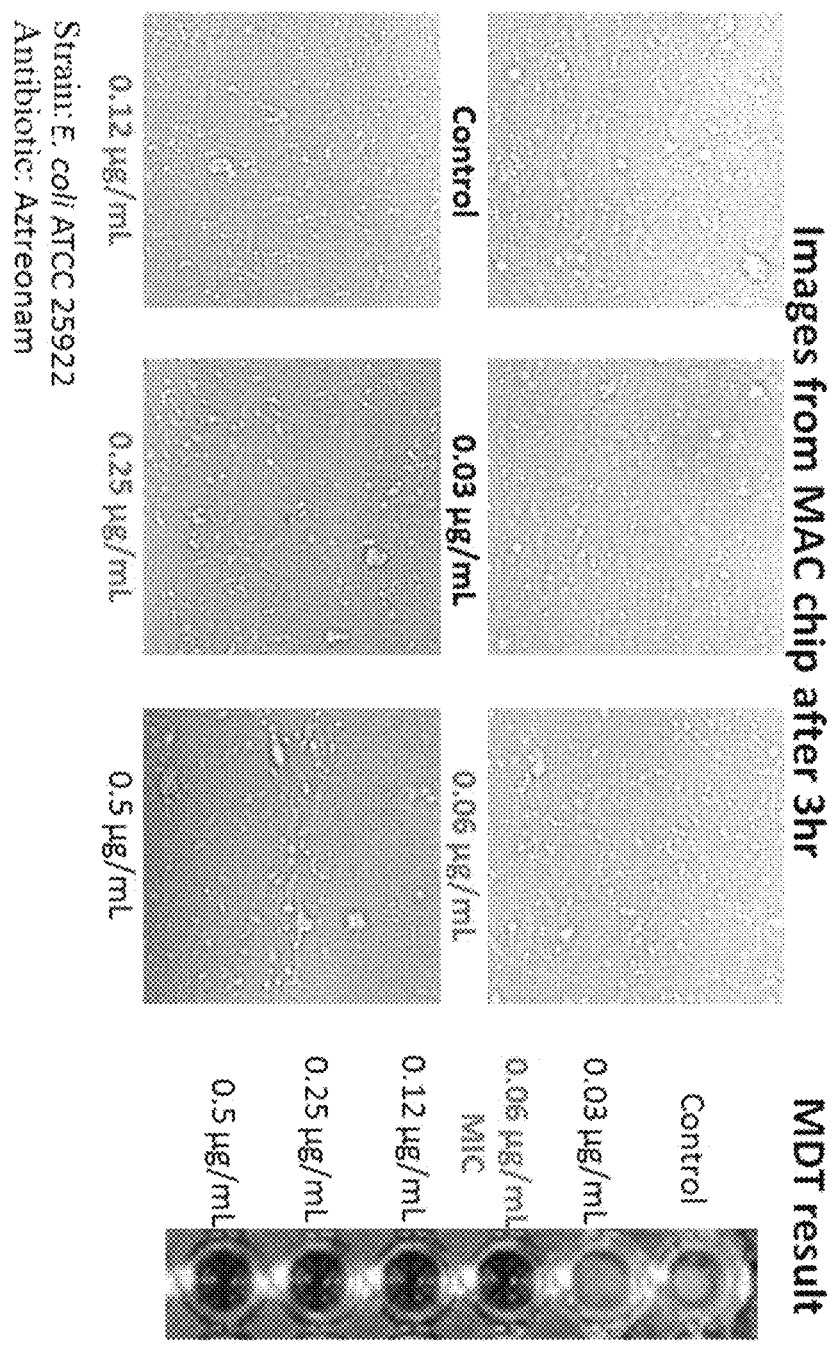

[Fig. 9]
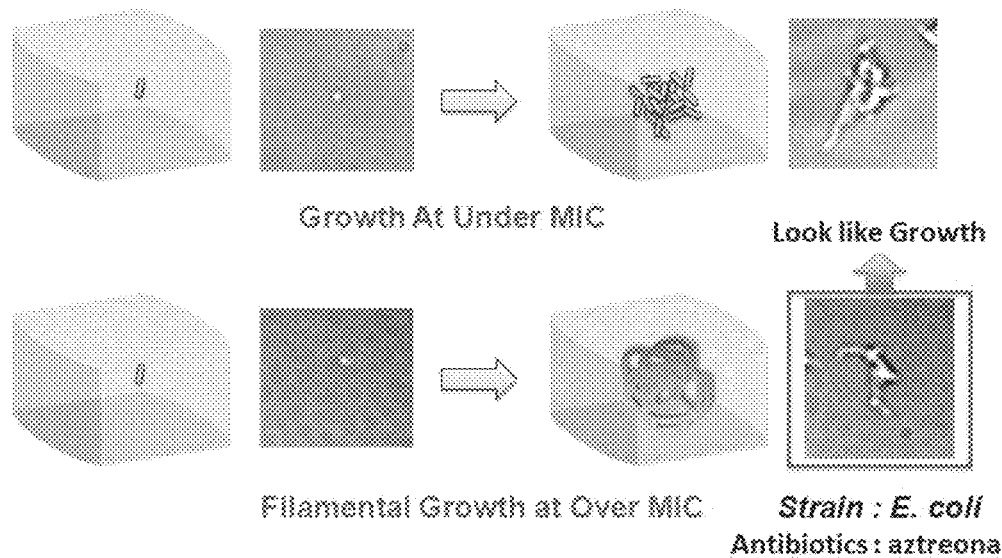
[Fig. 10]
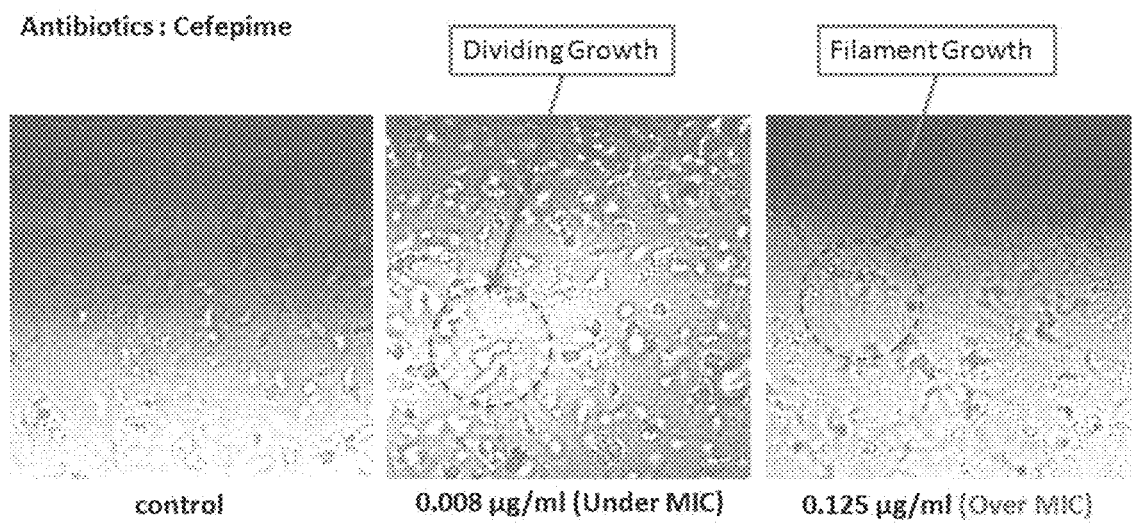

[Fig. 11]
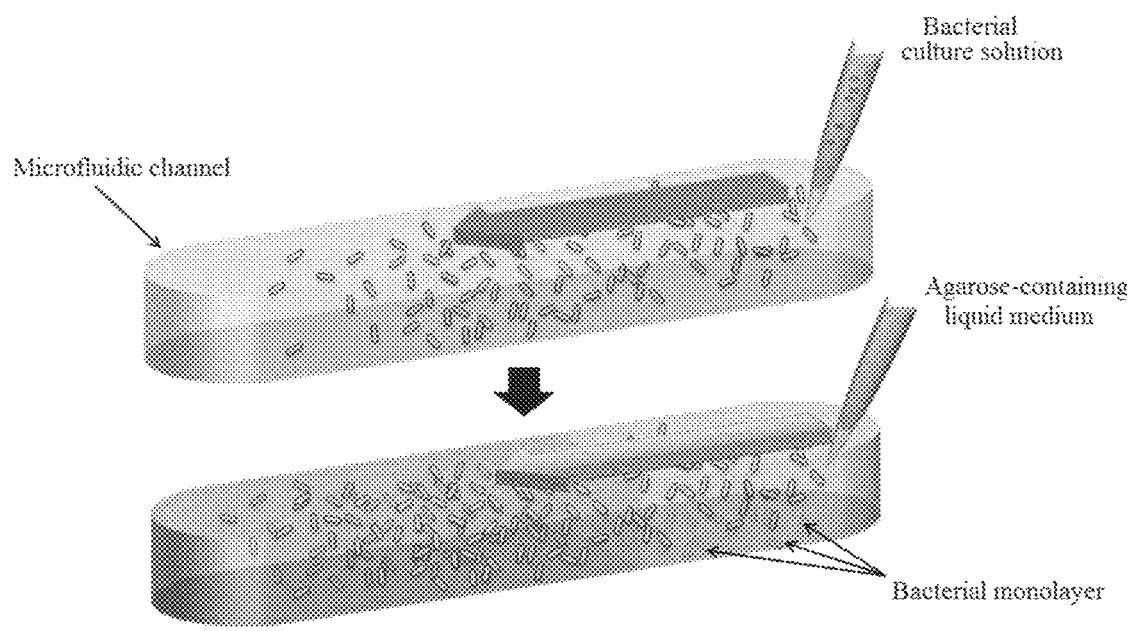
[Fig. 12]
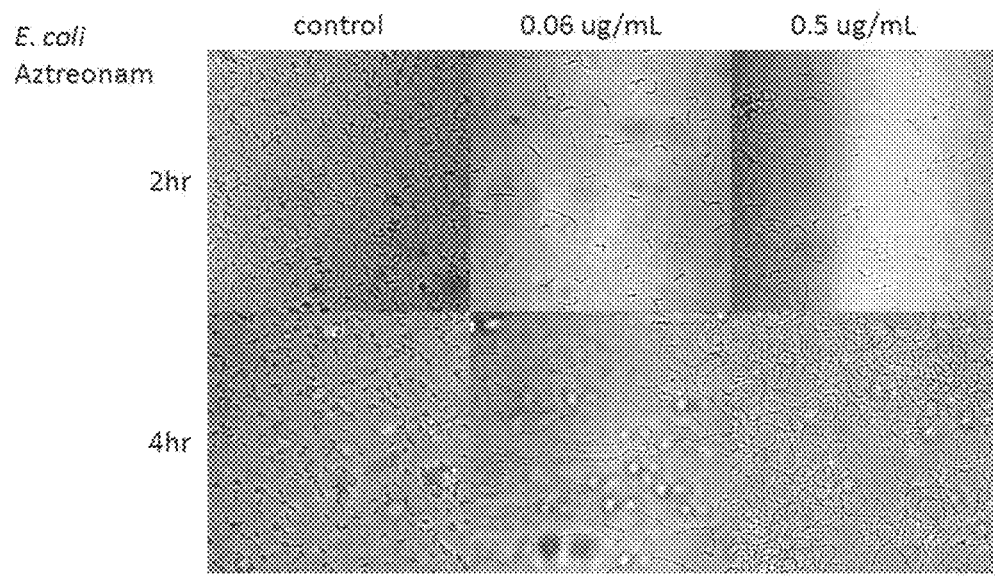

[Fig. 13]
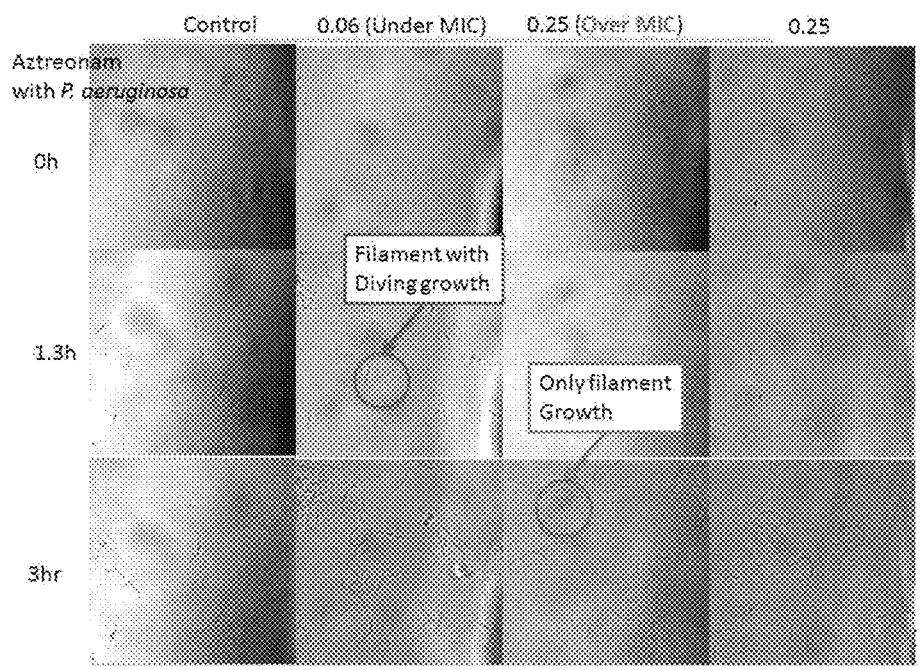
[Fig. 14]
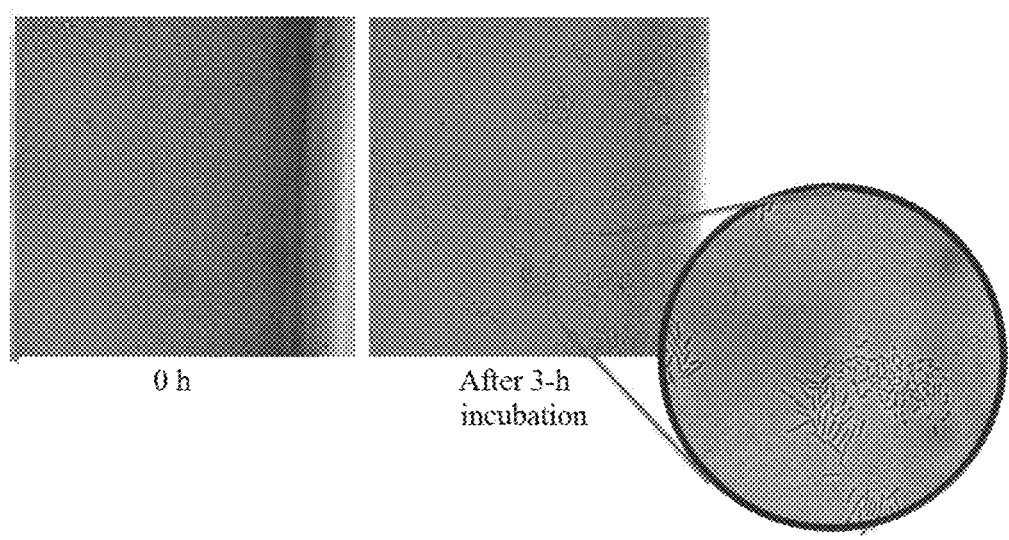

[Fig. 15]
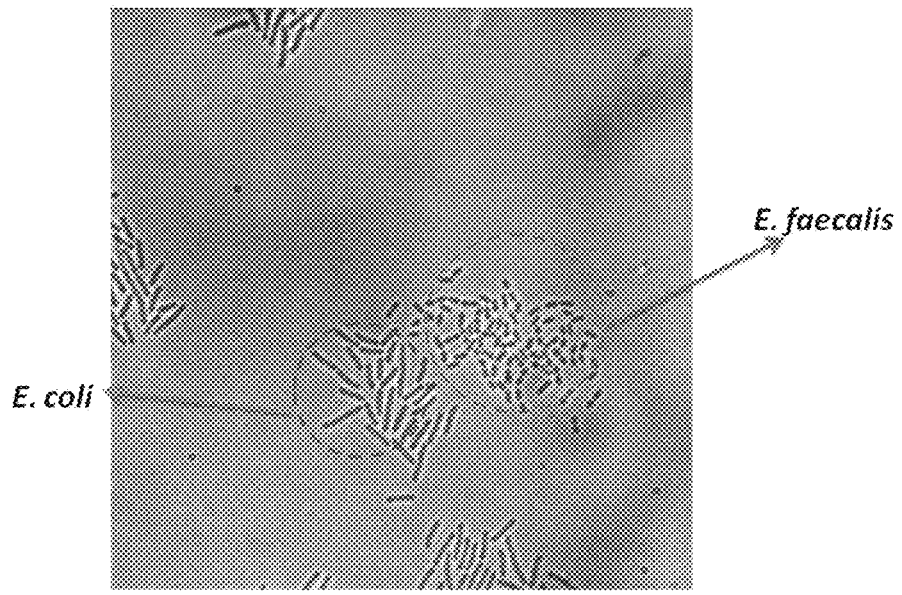
[Fig. 16]
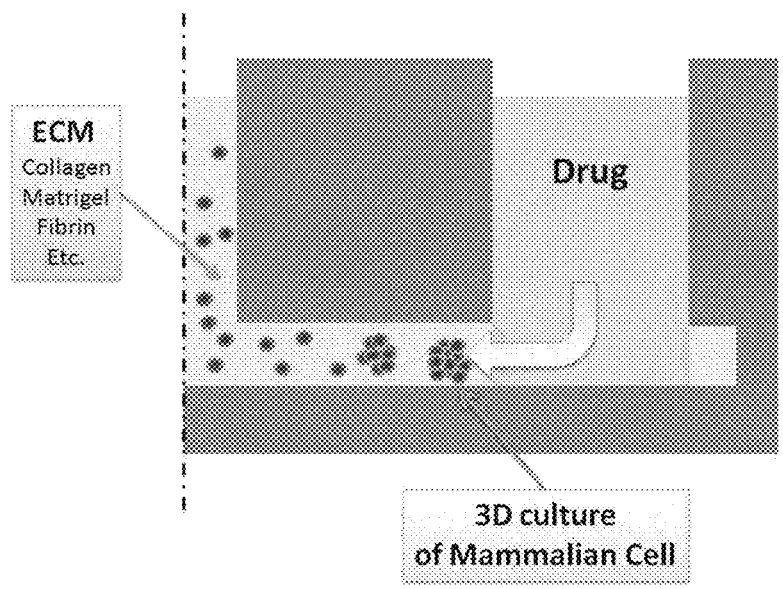

[Fig. 17]

| Gram-negative strain | E. coli ATCC 25922 | | P. aeruginosa ATCC 27853 | |
|---|---|---|---|---|
| Antibiotic | MAC | QC range | MAC | QC range |
| Amikacin | 0.5–1 | 0.5–4 | 1–2 | 1–4 |
| Amoxicillin/Clavulanic Acid | 4/2 | 2/1–8/4 | - | - |
| Ampicillin | 2–4 | 2–8 | - | - |
| Aztreonam | 0.12 | 0.06–0.25 | 2–4 | 2–8 |
| Cefazolin | 2 | 1–4 | - | - |
| Cefepime | 0.03–0.06 | 0.015–0.12 | 0.5–2 | 0.5–4 |
| Cefotaxime | 0.06 | 0.03–0.12 | 16 | 8–32 |
| Cefoxitin | 2 | 2–8 | - | - |
| Ceftazidime | 0.5 | 0.06–0.5 | 2–4 | 1–4 |
| Ciprofloxacin | 0.004–0.008 | 0.004–0.015 | 0.25–0.5 | 0.25–1 |
| Gentamicin | 0.25 | 0.25–1 | 0.5–1 | 0.5–2 |
| Imipenem | 0.12 | 0.06–0.25 | 1 | 1–4 |
| Norfloxacin | 0.03–0.06 | 0.03–0.12 | - | - |
| meropenem | - | - | 1 | 0.25–1 |
| Piperacillin | 2 | 1–4 | 4–8 | 1–8 |
| Piperacillin/Tazobactam | 1/4–2/4 | 1/4–4/4 | 2/4–8/4 | 1/4–8/4 |
| Tetracycline | 1 | 0.5–2 | - | - |
| Trimethoprim/Sulfamethoxazole | ≤0.5/9.5 | ≤0.5/9.5 | - | - |
| Ticarcillin | - | - | 16 | 8–32 |
| Ticarcillin/Clavulanic acid | - | - | 16/2 | 8/2–32/2 |
| Tobramycin | - | - | 0.25–0.5 | 0.25–1 |
| Measurement time | 3 hr | 16–20 hr | 3 hr | 16–20 hr |

| Gram-positive strain | S. aureus ATCC 29213 | | E. faecalis ATCC 29212 | |
|---|---|---|---|---|
| Antibiotic | MAC | QC range | MAC | QC range |
| Ampicillin | 1 | 0.5–2 | 0.5–1 | 0.5–2 |
| Amoxicillin/Clavulanic Acid | 0.25/0.12–0.5/0.25 | 0.12/0.06–0.5/0.25 | - | - |
| Ciprofloxacin | 0.5 | 0.12–0.5 | 0.5–2 | 0.25–2 |
| Clindamycin | 0.12 | 0.06–0.25 | - | - |
| erythromycin | 0.25 | 0.25–1 | 1 (6hr) | 1–4 |
| Gentamicin | 0.25–0.5 | 0.12–1 | ≤500 | ≤500 |
| Imipenem | 0.03 | 0.015–0.06 | - | - |
| Levofloxacin | 0.12–0.25 | 0.06–0.5 | 1 | 0.25–2 |
| Linezolid | 1–4 | 1–4 | 1–2 | 1–4 |
| Oxacillin | 0.5 | 0.12–0.5 | - | - |
| Norfloxacin | - | - | 2–4 | 2–8 |
| Penicillin | 0.5 | 0.25–2 | 1–2 | 1–4 |
| Rifampin | 0.004–0.008 (6 hr) | 0.004–0.015 | 0.5 | 0.5–4 |
| Streptomycin High Level | - | - | ≤500 | ≤500 |
| Teicoplanin | - | - | 0.5 | 0.25–1 |
| Tetracycline | 0.12–0.5 | 0.12–1 | 8 (6 hr) | 8–32 |
| Trimethoprim/sulfamethoxazole | ≤0.5/9.5 | ≤0.5/9.5 | - | - |
| Vancomycin | 1 | 0.5–2 | 2–4 | 1–4 |
| Measurement time | 4 hr | 16–20 hr | 4 hr | 16–20 hr |

MICROFLUIDIC MULTI-WELL-BASED CELL CULTURE TESTING DEVICE

CROSS-REFERENCE TO RELATED APPLICATIONS

This application is the U.S. National Phase under 35 U.S.C. § 371 of International Application No. PCT/KR2014/003977 filed on May 2, 2014, which in turn claims the benefit of Korean Application No. 10-2013-0049681, filed on May 2, 2013, the disclosures of which are incorporated by reference into the present application.

TECHNICAL FIELD

The present disclosure relates generally to a microfluidic multi-well-based cell culture testing device.

BACKGROUND ART

In general, the responses of cells to a drug are observed by placing the cells in a multi-well plate, injecting the drug in the form of a liquid, and monitoring time-dependent changes of the cells using an optical measurement system to obtain statistic results. As an antibiotic susceptibility testing method in a solid medium, Kirby-Bauer (KB) testing is known in which bacteria are scattered over an agar medium, antibiotic-absorbed papers are placed thereon, and bacterial growth is observed. In the case of microdilution testing in liquid media, a number of automated systems, such as VITEK2, Microscan, and Phoenix, have been developed for antibiotic susceptibility testing. Such a system can be used for antibiotic susceptibility testing by placing an antibiotic in millimeter-sized wells, injecting bacteria, together with a liquid medium, into the wells, and statistically monitoring and determining the bacterial growth through turbidity.

When the responses of cells to different drugs are tested using the conventional systems, the cells are placed in a liquid or solid medium, the drugs are mixed with the liquid medium or drug-absorbed paper disks are placed on the solid medium to allow the cells to respond to the drugs, and the cell growth responses to the drugs are determined by turbidity (absorbance) measurement. However, such an approach is dependent on the collection of statistically valid data rather than on changes of single cells, and requires a long incubation time (usually 16-24 hours) because at least a predetermined number of cells should grow (usually one million cells per ml) in order to obtain statistic results. In this case, it is impossible to monitor changes occurring in single cells against drugs and monitor motile single cells in real time. Further, a great deal of time and labor is required to test the large number of drugs because the individual drugs are injected separately. The KB-test for antibiotic susceptibility testing in solid media basically requires a large number of agar medium plates to test the susceptibility of tens of antibiotics due to the limited number of the drugs that can be placed on the solid media. VITEK, an automated system developed to minimize testing time, also requires a relatively long time of about 12 hours because the turbidity of bacteria should increase above a predetermined level. Further, since environments for the conventional testing methods are different from in vivo environments, there may be many substantial differences between the test results and phenomena occurring in vivo (Gregory G. Anderson, et al. (2003), "Intracellular Bacterial Biofilm-Like Pods in Urinary Tract Infections", *Science* 301, 105; Gallo et al. (2011), "Demonstration of *Bacillus cereus* in Orthopaedic-Implant-Related Infection with Use of a Multi-Primer Polymerase Chain Reaction-Mass Spectrometric Assay.", J Bone Joint Surg Am, 93).

Thus, there is a need to develop an accurate and rapid technique for antibiotic susceptibility testing compared to conventional techniques.

DETAILED DESCRIPTION OF THE INVENTION

One aspect of the present invention provides a microfluidic multi-well-based cell culture testing device that has an array structure of a plurality of aligned microfluidic well units, each of the microfluidic well units includes an inlet through which a first fluid enters, an accommodation compartment adapted to accommodate a second fluid therein, a microfluidic channel through which the first fluid flows, and an air outlet adapted to facilitate the entering of the first fluid, wherein the microfluidic channel is in communication with the inlet and the air outlet such that the first fluid is allowed to flow into and fill the microfluidic channel, wherein the accommodation compartment is designed in the form of a well such that the entering second fluid is retained, and a capillary valve is formed where a portion of the lower lateral side of the accommodation compartment is in communication with a portion of the lateral side of the microfluidic channel such that the first fluid and the second fluid meet each other to form an interface.

According to one embodiment, the dimensions of the microfluidic well unit may correspond to those of each of the wells of a commercial multi-well plate.

According to one embodiment, each of the wells may be arranged in a 1×1, 1×2, 1×4, 2×4, 4×6, 12×8, 24×16 or 48×32 matrix.

According to one embodiment, the microfluidic channel may be arranged to surround the accommodation compartment such that the microfluidic well unit has a quadrangular structure.

According to one embodiment, the capillary valve may have a predetermined thickness and width to prevent the first fluid from entering the accommodation compartment.

A further aspect of the present invention provides a cell analysis method using a microfluidic multi-well-based cell culture testing device having an array structure of a plurality of aligned microfluidic well units. Each of the microfluidic well units includes an inlet through which a mixture solution of a gelling agent-containing liquid medium and a biological agent enters, an accommodation compartment adapted to accommodate a physiologically active substance therein, a microfluidic channel in communication with the inlet and through which the liquid medium flows, and a capillary valve through which a portion of the lower lateral side of the microfluidic channel is in communication with a portion of the lateral side of the accommodation compartment. The cell analysis method includes the steps of (a) introducing the mixture solution of the gelling agent-containing liquid medium and the biological agent into the inlet to fill the mixture solution in the microfluidic channel and gelling the mixture solution to form a solid thin film, (b) feeding the physiologically active substance into the accommodation compartment and diffusing the physiologically active substance into the solid thin film through the capillary valve, and (c) observing changes of the biological agent occurring at an interface where the mixture solution and the physiologically active substance meet each other, on a single cell basis.

According to one embodiment, step (a) may include (a-1) introducing a solution containing the biological agent into the inlet to fill a portion of the microfluidic channel and (a-2) further introducing the gelling agent-containing liquid medium into the inlet to allow the liquid medium to form a laminar flow and to fill the microfluidic channel, so that a monolayer of the biological agent is formed on the upper and lower wall surfaces of the microfluidic channel.

According to one embodiment, the cell analysis method may further include a step of (d) observing the responses of the biological agent to the physiologically active substance on a single cell basis to determine the minimum inhibitory concentration (MIC) or minimum biofilm eradication concentration (MBEC) of the physiologically active substance.

BRIEF DESCRIPTION OF THE DRAWINGS

FIGS. 1 and 2 illustrate a microfluidic multi-well-based cell culture testing device according to one embodiment of the present invention.

FIG. 3 is a cross-sectional view of a microfluidic well unit.

FIG. 4 is a conceptual diagram showing an imaging procedure using a cell culture testing device with a 96-well chip design.

FIG. 5 shows a procedure for antibiotic susceptibility testing using a cell culture testing device according to one embodiment of the present invention.

FIG. 6 shows images of experimental results demonstrating that the MIC values of penicillin antibiotic for an *E. faecalis* strain could be rapidly determined using a MAC chip.

FIG. 7 shows images showing the shapes of biofilms responding to an antibiotic, which were investigated using a MAC chip according to one embodiment of the present invention.

FIG. 8 shows the growth of a gram-negative bacterial species in agarose in the presence of a β-lactam antibiotic at different concentrations in a state in which the agarose was mixed with a solution of the bacteria.

FIG. 9 is a detailed diagram explaining the phenomena shown in FIG. 8.

FIG. 10 shows the occurrence of the phenomena explained in FIG. 9 in an *E. coli* strain in the presence of a β-lactam antibiotic.

FIG. 11 shows a procedure for introducing raw materials into a microfluidic channel to obtain an image of a monolayer of bacteria.

FIG. 12 shows images showing the growth of a bacterial species in the presence of an antibiotic at different concentrations in a state in which the bacteria were formed into a monolayer.

FIG. 13 shows images showing the growth of a *P. aeruginosa* strain in the presence of aztreonam as a β-lactam antibiotic at concentrations under and over MIC.

FIGS. 14 and 15 are optical microscopy images showing the growth of two bacterial strains without an antibiotic and two bacterial strains resistant to an antibiotic, revealing that double infection with the bacterial strains could be measured.

FIG. 16 is a diagram showing 3D culture of mammalian cells using a cell culture testing device according to one embodiment of the present invention.

FIG. 17 shows MIC values for 4 species of clinical strains, as measured by single-cell morphological analysis (SCMA) using a MAC chip.

MODE FOR CARRYING OUT THE INVENTION

Embodiments of the present invention will now be described in more detail with reference to the accompanying drawings. However, the present invention is not limited to the embodiments set forth herein and may be embodied in many different forms. Rather, these embodiments are provided so that this disclosure is thorough and complete, and will fully convey the scope of the invention to those skilled in the art. In the drawings, the sizes, such as widths and thicknesses, of elements may be exaggerated for clarity. The drawings are explained entirely from an observer's point of view. It will be understood that when an element is referred to as being "on" another element, it can be directly on the other element or one or more intervening elements may also be present therebetween. Those skilled in the art will appreciate that many modifications and variations can be made without departing from the spirit of the invention. Throughout the accompanying drawings, the same reference numerals are used to designate substantially the same elements.

On the other hand, terms used herein are to be understood as described below. The terms "first", "second," etc. are used only to distinguish one element from another and the scope of the claims should not be limited by these terms. For example, a first element could be termed a second element, and, similarly, a second element could be termed a first element.

As used herein, the singular forms "a", "an" and "the" are intended to include the plural forms as well, unless the context clearly indicates otherwise. It will be further understood that the terms "include(s)", "including", "have (has)" and/or "having", when used in this specification, specify the presence of stated features, integers, steps, operations, elements, and/or components, but do not preclude the presence or addition of one or more other features, integers, steps, operations, elements, components, and/or groups thereof. Respective steps of the methods described herein may be performed in a different order than that which is explicitly described. In other words, the respective steps may be performed in the same order as described, simultaneously, or in a reverse order.

FIGS. 1 and 2 illustrate a microfluidic multi-well-based cell culture testing device according to one embodiment of the present invention. Specifically, FIGS. 1 and 2 are top and bottom perspective views of the microfluidic multi-well-based cell culture testing device, respectively.

Referring to FIG. 1, the cell culture testing device 100 has outwardly open inlets 120, accommodation compartments 130, and air outlets 150, as viewed from the top. Due to this structure, first and second fluids can be introduced into the cell culture testing device 100. Referring to FIG. 2, unlike the top structure, the cell culture testing device 100 has a structure blocked from the outside, as viewed from the bottom. Due to this structure, the first and second fluids can be accommodated in the cell culture testing device 100.

Referring to FIGS. 1 and 2, the microfluidic multi-well-based cell culture testing device 100 has an array structure of a plurality of aligned microfluidic well units 110. Each of the microfluidic well units 110 includes an inlet 120 through which a first fluid enters, an accommodation compartment 130 adapted to accommodate a second fluid therein, a microfluidic channel 140 through which the first fluid flows, and an air outlet 150 adapted to facilitate the entering of the first fluid. The aligned microfluidic well units 110 may have dimensions corresponding to the dimensions of the wells of a commercial multi-well plate as a whole. Preferably, the centers of the microfluidic well units 110 match those of the wells of a commercial multi-well plate.

Multi-well plates are standard tools for treating and analyzing a number of samples in chemical, biochemical and/or biological assays. Multi-well plates may take various forms, sizes, and shapes. Generally, multi-well plates are manufactured to have standard sizes and shapes and have standard arrangements of wells. The standard arrangements of wells include those found in 96-well plates (12×8 array of wells), 384-well plates (24×16 array of wells), and 1536-well plates (48×32 array of wells). Multi-well plates having other arrangements of wells are commercially available.

Since the cell culture testing device 100 has dimensions similar to the dimensions of commercial multi-well plates, it is easily interchangeable with commercial multi-well plates for various conventional biological analysis techniques.

Each of the first and second fluids may include 80% or more by weight of water or 90% or more by weight of water as a dispersion medium or a solvent. For example, the first fluid may be a mixture solution of a gelling agent-containing liquid medium and a biological agent. The second fluid may be an aqueous solution containing a physiologically active substance. The first fluid enters through the outwardly open inlets 120 formed in the top portion of the cell culture testing device 100. Likewise, the second fluid enters the cell culture testing device 100 through upper openings of the accommodation compartments 130. The second fluid may be introduced using a special pump or by pipetting.

Each of the accommodation compartments 130 is designed in the form of a well that has a space whose size is sufficient to retain the entering second fluid. The volume of the well is not particularly limited so long as it is sufficient to observe reactions for a long time after the second fluid enters. The volume of the well is preferably from 100 µl to 2000 µl.

Each of the microfluidic channels 140 is in communication with the inlet 120 and the air outlet 150 such that the first fluid is allowed to flow into and fill the microfluidic channel 140. For example, the microfluidic channel 140 may have a width of hundreds of µm to several mm and a depth (or thickness) of hundreds of µm. With these dimensions, subsequent imaging is easy to perform and the first fluid can fill the microfluidic channel 140 by capillary action. In the case where the first fluid is a liquid medium containing a gelling agent, the first fluid may be gelled after the lapse of a predetermined time, resulting in the formation of a solid thin film that fills the microfluidic channel 140.

A portion of the lower lateral side of the accommodation compartment 130 is in communication with a portion of the lateral side of the microfluidic channel 140 such that the first fluid and the second fluid meet each other to form an interface.

Preferably, the body of the cell culture testing device 100 is made of a transparent material so that phenomena occurring in the cell culture testing device 100 can be easily observed. The transparent material is preferably a polymer resin, such as polystyrene, polyethylene, polypropylene, polymethacrylate or polycarbonate. The cell culture testing device 100 may be manufactured by injection molding the polymer resin.

FIG. 3 is a cross-sectional view of the microfluidic well unit. Referring to FIG. 3, the microfluidic well unit 110 has a structure close to a quadrangle as a whole, whose dimensions are similar to the dimensions of each well of a commercial multi-well plate. For example, the microfluidic well unit 110 has a square structure. The microfluidic channel 140 surrounds the accommodation compartment 130 and is elongated as much as possible. This structure increases the amount of the entering first fluid. Due to this advantage, the sample is easy to handle. The microfluidic channel 140 is closed at one end but is in communication with the air outlet 150 such that the first fluid entering through the inlet 120 flows into and easily fills the microfluidic channel 140. The first fluid may be a liquid medium containing a gelling agent, such as agarose. The first fluid may include a biological agent, such as a bacterial strain. A capillary valve 160 is formed where the microfluidic channel 140 is in communication with the accommodation compartment 130. When the first fluid fills the microfluidic channel 140 by capillary action, the presence of the capillary valve 160 enables the formation of an interface between the first fluid and the second fluid while preventing the first fluid from entering the accommodation compartment 130. That is, the thickness and width of the capillary valve 160 are controlled such that the capillary action is maintained. The capillary valve 160 typically has a thickness of 100 to 500 µm and a width of 500 µm to 2 mm. Within these ranges, the first fluid is prevented from overflowing into the accommodation compartment 130 and can fill the microfluidic channel 140. The air outlet 150 formed at one end of the microfluidic channel 140 is in communication with the upper wall of the microfluidic channel 140 and is exposed to the atmosphere. With this arrangement, when the first fluid fills the microfluidic channel 140, air present in the microfluidic channel 140 is released to the atmosphere through the air outlet 150.

FIG. 4 is a conceptual diagram showing an imaging procedure using the cell culture testing device with a 96-well chip design. In some embodiments, an agarose solution as the first fluid is introduced into the microfluidic channel. For this reason, the cell culture testing device according to one embodiment of the present invention can also be called a "microfluidic agarose channel (MAC) chip".

Referring to FIG. 4, an agarose solution containing bacteria is introduced through the inlet of the cell culture testing device to fill the microfluidic channel. The agarose solution is then gelled. Thereafter, an antibiotic solution is introduced through the accommodation compartment. At this time, the gelled agarose and the antibiotic solution form an interface at the junction of the microfluidic channel and the accommodation compartment. Next, the antibiotic crosses the interface, diffuses to the gelled agarose, and meets the bacteria. Since the gelled agarose as a whole forms a solid thin film, the bacteria are immobilized in the thin film. This immobilization enables the observation of the reactivity of the bacteria on a single cell basis through an imaging system. Further details will be provided below.

FIG. 5 shows a procedure for antibiotic susceptibility testing using the cell culture testing device according to one embodiment of the present invention.

First, a liquid medium containing a gelling agent is mixed with a biological agent to prepare a mixture solution.

The liquid medium comprises water in an amount of about 95% or more. The liquid medium can be solidified due to the presence of the gelling agent. As the gelling agent, there may be exemplified agar, agarose, gelatin, alginate, collagen or fibrin. The use of agar or agarose is preferred. For example, agar may be used in an amount of 0.5 to 4% by weight in the liquid medium. The liquid medium usually requires no nutrients. In some examples, however, the liquid medium may include nutrients.

Examples of biological agents suitable for use in the present invention include viruses, bacteria, fungi, algae, protozoa, parasitic pathogens, human and mammalian cells, and biofilms. The biological agent may grow in a liquid or solid medium, and the growth thereof may be affected by the kind and concentration of a foreign physiologically active substance. The density of the biological agent in the mixture solution is from $10^2$ to $10^{10}$ cells/ml, preferably from $10^4$ to $10^{10}$ cells/ml, more preferably from $10^5$ to $10^9$ cells/ml. If the density of the biological agent is below the lower limit defined above, it may be difficult to perceive the location of the biological agent. Meanwhile, if the density of the biological agent exceeds the upper limit defined above, it may be difficult to perceive the individual state of the biological agent.

Next, a predetermined amount (e.g., 10-12 μl) of the mixture solution is introduced through the inlet. Then, the bacteria-containing agarose moves along the channel. As the channel is filled with the mixture solution, air escapes from the channel through the air outlet, which facilitates the introduction of the mixture solution into the channel.

The mixture solution is gelled to form a solid thin film in which the biological agent is immobilized. When the liquid medium is cooled to a lower temperature, the medium is gelled, and as a result, the movement of the biological agent is slowed down. This immobilization facilitates continuous observation of the motile biological agent.

The cell culture testing device is preferably made of a transparent material for optical imaging. The liquid medium may be applied to and gelled in each microfluidic channel of the cell culture testing device to form a solid thin film. The liquid medium is fed through the inlet and undergoes gelling in the microfluidic channel. The thickness of the solid thin film may be determined depending on the depth of the microfluidic channel. The depth of the microfluidic channel may be in the range of 1 μm to 5 mm, 1 μm to 3 mm, 1 μm to 2 mm, 1 μm to 1.5 mm, 1 μm to 1 mm, 1 μm to 800 μm, 1 μm to 500 μm, 1 μm to 100 μm, 10 μm to 3 mm, 100 μm to 500 μm, 10 μm to 1 mm, 100 μm to 1 mm, 200 μm to 1 mm, 500 μm to 1 mm, or 100 μm to 500 μm. The depth of the microfluidic channel is preferably from 100 μm to 500 μm.

When the size of an imaging area is taken into consideration, the width of the microfluidic channel may be from 100 μm to 5 mm, 300 μm to 5 mm, 500 μm to 3 mm, or 1 mm to 3 mm. The width of the microfluidic channel is preferably from 1 mm to 3 mm.

There is no particular restriction on the shape and length of the microfluidic channel. It is preferred that the largest possible amount of the mixture solution of the gelling agent-containing liquid medium and the biological agent is introduced into the microfluidic channel while maintaining the dimensions and width of the microfluidic channel. This facilitates accurate control over reactions with the antibiotic. Preferably, each microfluidic well unit has dimensions corresponding to the size of each well of a commercial multi-well plate and the microfluidic channel surrounds the accommodation compartment such that it is elongated as much as possible.

The thickness and width of the solid thin film are determined depending on the depth and width of the microfluidic channel. The term "thin film" used herein refers to a thin layer that has a thickness sufficient to immobilize the biological agent and to observe the biological agent on a single cell basis. The thickness of the thin film is typically in the range of 1 μm to 5 mm, 1 μm to 3 mm, 1 μm to 2 mm, 1 μm to 1.5 mm, 1 μm to 1 mm, 1 μm to 800 μm, 1 μm to 500 μm, 1 μm to 100 μm, 10 μm to 3 mm, 100 μm to 500 μm, 10 μm to 1 mm, 100 μm to 1 mm, 200 μm to 1 mm, or 500 μm to 1 mm, but is not particularly limited to this range. The thickness of the solid thin film may correspond to the size of a side of the solid thin film in a direction perpendicular to a side of the solid thin film to be observed. When the thickness of the solid thin film is in the range defined above, the biological agent immobilized in the solid thin film can be observed on a single cell basis.

Next, a physiologically active substance is introduced into the accommodation compartment through an opening of the accommodation compartment and is allowed to diffuse into the solid thin film. The physiologically active substance may include a substance selected from drugs, such as antibiotics, anticancer agents and immunosuppressants, nutrients, cellular secretions, signal transducers, viruses, cells, microRNAs, proteins, antigens, antibodies, and DNA. It is desirable that the accommodation compartment is large enough to accommodate a sufficient amount of the physiologically active substance. For example, the accommodation compartment may have a diameter of about 3 mm to about 15 mm and a height of about 3 mm to about 15 mm. With these dimensions, the reactions of the raw materials can be easily observed after one-time injection of the raw materials while maintaining the reactions for a long time.

Next, the responses of the biological agent to the physiologically active substance are observed. The biological agent is immobilized and distributed two-dimensionally in the solid thin film, and as a result, it can be observed on a single cell basis. Changes in the growth of the single cells can be typically observed within several tens of minutes (normally 30 minutes). Accordingly, the use of the cell culture testing device according to the present invention allows for accurate and rapid identification of the effect of the physiologically active substance on the biological agent compared to the use of conventional cell culture testing devices. For example, physiological activity testing on bacterial cells can be completed within 3-4 hours. Herein, such a rapid physiological activity testing method is called "single-cell morphological analysis (SCMA)". The use of the MAC system enables observation of changes in single-cell morphology in the presence of various antibiotics by time-lapse imaging.

An optical measurement system may be used for observation. The optical measurement system may include an imaging system, such as a CCD or CMOS camera. The optical measurement system may include optical units or devices necessary for focusing and light imaging, such as a lens, an illuminator, and a light guide. The optical measurement system may include an image processing system for processing and analyzing image data observed by the imaging system. The optical measurement system rapidly records and analyzes changes in the growth of the biological agent observed during testing to obtain test results. An imaging area is obtained from the vicinity of the interface between the microfluidic channel and the accommodation compartment. The imaging area may have a size of about 300 μm*300 μm to about 500 μm*500 μm. The width of the microfluidic channel is at least larger than that of the imaging area.

Consequently, the use of the culture testing device according to the present invention based on the immobilization of the biological agent and the diffusion of the physiologically active substance can greatly reduce the amounts of drugs and cells necessary for drug testing, and enables rapid tracking of changes in the growth of single cells to obtain test results on the drugs as rapidly as 2 hours (normally within 3-4 hours), compared to the prior art. This is the most rapid testing speed known thus far.

FIG. 6 shows images of experimental results demonstrating that the MIC values of penicillin antibiotic for an *E. faecalis* strain could be rapidly determined using the MAC chip. For this experiment, an *E. faecalis* solution was homogenized with liquid agarose and was injected into the chip. The agarose was gelled at room temperature. Thereafter, liquid penicillin as an antibiotic was injected into the well spaces. The chip was then incubated at an incubator at 37° C. and the results were observed after 4-h incubation.

The susceptibility test results obtained using the antibiotic at various concentrations of 0.5 to 8 µg/ml are shown in FIG. 6. The MIC of penicillin (2 µg/ml) could be obtained in 4 hours. In contrast, according to micro-dilution testing (MDT), a much longer time (18 hours) was consumed to obtain the MIC of penicillin.

The use of the microfluidic channels can reduce the necessary amounts of the biological agent and the physiologically active substance, enabling physiological activity testing at reduced cost. Another advantage associated with the use of the microfluidic channel system is that the responses of a single biological agent to various kinds and concentrations of physiologically active substances can be observed simultaneously.

The MAC chip can be very useful for biofilm assay as well as antibiotic susceptibility testing. Biofilms are found in areas infected with microbes or to which microbes are attached. Biofilms refer to films that constitute mucilaginous microbial complexes, which are formed by microbes surrounded with polymer matrices. The formation of biofilms can greatly affect human health. Biofilms cause pulmonary infections, otitis media, periodontitis, and other infectious diseases. The resistance of bacteria present in biofilms against antibiotics is at least 1,000 times stronger than that of suspended bacteria. Flow cell systems and well-based systems have been used to investigate biofilms. However, these assay systems require a long time of several days for biofilm formation. Other difficulties associated with the use of the assay systems are the need to stain biofilms and the use of confocal microscopes for observation. Further experiments are needed for the measurement of minimum inhibitory concentration (MIC) or minimum biofilm eradication concentration (MBEC). Such systems are very large in size and fail to clearly show biofilm formation stages and to represent in vivo biofilm formation.

Thus, there is a need for efficient systems that are suitable to investigate the formation of biofilms and the reactivity of biofilms with antibiotics. In consideration of this need, the MAC chip according to one embodiment of the present invention proves to be an excellent alternative to conventional systems.

FIG. 7 shows images showing the shapes of biofilms responding to an antibiotic, which were investigated using the MAC chip according to one embodiment of the present invention. For this experiment, an *E. faecalis* solution was homogenized with liquid agarose and was injected into the chip. The agarose was gelled at room temperature. Thereafter, liquid penicillin as an antibiotic was injected into the accommodation compartments of the MAC chip. The chip was then incubated at an incubator at 37° C. and the results were observed after 4-h incubation. The bacteria were immobilized by the surrounding agarose. In this state, the bacteria were continuously divided to form bacterial populations, which constitute a biofilm.

A certain species of bacteria grows into filaments in the presence of a specific antibiotic at a concentration over the MIC. This filamental growth is not clearly distinguished from the division of the bacteria, which looks like growth. Thus, there may be difficulty in determining the MIC.

FIG. 8 shows the growth of a gram-negative bacterial species in agarose in the presence of a β-lactam antibiotic at different concentrations in a state in which the agarose was mixed with a solution of the bacteria. It can be observed from FIG. 8 that the bacteria still grew even at concentrations over the MIC. In the MDT results, however, the growth of the bacteria was observed to be inhibited at 0.06 µg/ml.

FIG. 9 is a detailed diagram explaining the phenomena shown in FIG. 8. In this experiment, an antibiotic was injected in a state in which bacteria were mixed with agarose. The antibiotic was adjusted to have concentrations under and over the MIC. The results show filamental growth of the bacteria at over the MIC (bottom of FIG. 9) and dividing growth of the bacteria at under the MIC (top of FIG. 9), which looks like the filamental growth. FIG. 10 shows the occurrence of the phenomena explained in FIG. 9 in an *E. coli* strain in the presence of a β-lactam antibiotic. The dividing growth of the bacteria at under the MIC was not distinguished from the filamental growth of the bacteria at over the MIC, causing difficulty in determining the MIC. Therefore, the formation of a monolayer of the bacteria in an imaging area would enable more precise observation.

According to one embodiment of the present invention, there is provided an antibiotic susceptibility testing method by which a single focus monolayer can be observed.

Generally, when a homogenous mixture solution of bacteria and an agarose-containing liquid medium is introduced into each microfluidic channel, a certain number of the bacteria are stochastically present on the bottom of the channel to form a monolayer. Sequential introduction of the bacteria and the agarose-containing liquid medium as raw materials into each microfluidic channel is considered as a preferable approach to form a better monolayer.

FIG. 11 shows a procedure for introducing raw materials into the microfluidic channel to obtain an image of a monolayer of bacteria. Referring to FIG. 11, first, a bacterial culture solution is introduced into the microfluidic channel through the inlet of the cell culture testing device. At this time, it is preferred that a predetermined space of the microfluidic channel remains unfilled and only a portion of the channel is filled with the culture solution. For example, about one-third of the volume of the channel is filled with the culture solution, and then an agarose-containing liquid medium is further introduced into the microfluidic channel. Rapid introduction of the agarose-contain liquid medium creates a laminar flow of the liquid medium and causes the bacteria to gather on the wall surfaces of the channel (mainly on the upper and lower wall surfaces of the channel when the width and depth of the channel are taken into consideration). As a consequence, the bacteria can be distributed substantially in the form of a monolayer on the wall surfaces.

FIG. 12 shows images showing the growth of a bacterial species in the presence of an antibiotic at different concentrations in a state in which the bacteria were formed into a monolayer. The bacteria were divided at concentrations (control and 0.06 µg/mL) under the MIC whereas they grew only in the form of filaments at a concentration (0.5 µg/mL) over the MIC. From these observations, the MIC could be determined FIG. 13 shows images showing the growth of a *P. aeruginosa* strain in the presence of aztreonam as a β-lactam antibiotic at concentrations (control and 0.06 µg/mL) under the MIC and concentrations (0.25 and 0.5 µg/mL) over the MIC. The bacteria were divided to grow in the form of filaments under the MIC whereas they grew only in the form of filaments over the MIC. The MIC can be determined by observing the division of the bacteria in the images of the monolayers.

According to the present invention, cells can be observed by both single focus monolayer imaging and 3D imaging. That is, when a mixture of agarose as a gelling agent and bacterial cells is introduced into each channel, the cells can be observed in the form of a monolayer at the interface between the bottom plate of the MAC chip and the agarose and can be observed in the other portions after 3D culture.

Meanwhile, sequential addition of bacteria cells and a gelling agent (agarose) through one inlet leads to the formation of a monolayer of the bacteria, which can be observed by single focus imaging.

In addition, the use of the cell culture testing device according to the present invention enables observation of double infection by imaging.

FIGS. 14 and 15 are optical microscopy images showing the growth of two bacterial strains without an antibiotic and two bacterial strains resistant to an antibiotic, revealing that double infection with the bacterial strains could be measured.

The experimental conditions are as follows:
Strains
*E. coli* ATCC 25922 (rod-shaped strain)
*E. faecalis* ATCC 29212 (spherical strain)
Antibiotics
Gentamicin (concentration: 32 µg/mL)
MICs are in the susceptible range for both strains
Erythromycin (concentration: 8 µg/mL)
Susceptible to *E. faecalis* ATCC 29212 only
Control
Incubation time: 3 h
Strain concentration
McFarland 0.25
Agarose concentration: 2%
Observed using 100× magnification lenses The shapes of the bacteria were difficult to discern in the 0 h-images and could not be monitored until the bacteria were divided to some extent after the lapse of 4 h. At this time, the coexistence of the rod-shaped bacteria and the spherical bacteria was confirmed. It could also be confirmed whether double infection with the bacteria occurred.

FIG. 16 is a diagram showing 3D culture of mammalian cells using the cell culture testing device according to one embodiment of the present invention. For this experiment, a mixture of mammalian cells and an ECM (collagen, matrigel, fibrin, agarose, etc.) was introduced into the channel. After gelling of the ECM, a medium or a drug was injected. As a result, the cells were grown by nutrients supplied from the medium. Alternatively, the cells were killed by the drug. In such environments, the bacteria grew three-dimensionally, i.e. in 3D culture.

FIG. 17 shows MIC values for 4 species of clinical strains, as measured by single-cell morphological analysis (SCMA) using the MAC chip. Four strains, including *E. coli, E. faecalis, P. aeruginosa*, and *S. aureus*, from about 40 patients were obtained from Professor Seung-ok Lee (Department of diagnostic medicine, Incheon St. Mary's Hospital, The Catholic University of Korea). 60× objective lenses (40× lenses for *E. coli*) were used for microscopy. At Mc=0.5, each strain was mixed with agarose. The formation of a monolayer on the bottom was observed. The MIC value could be obtained using the MAC chip in 4 h. Referring to FIG. 17, the MIC values measured using the MAC chip were in good agreement with the MIC ranges (i.e. quality control ranges) defined by the Clinical and Laboratory Standards Institute (CLSI). Therefore, single cell morphological analysis using the MAC chip can be considered a very rapid and accurate AST assay.

Although the present invention has been described in detail with reference to the drawings and embodiments, those skilled in the art will appreciate that various variations and modifications can be made to the embodiments without departing from the spirit of the present invention as disclosed in the appended claims.

The invention claimed is:

1. A microfluidic multi-well-based cell culture testing device that has an array structure of a plurality of aligned microfluidic well units, each of the microfluidic well units comprising
    an inlet comprises a recess, wherein the recess is exposed to air in an upward direction such that a first fluid is injected into the inlet from a top of the recess,
    an accommodation compartment adapted to accommodate a second fluid therein,
    a microfluidic channel through which the first fluid flows, and
    an air outlet adapted to facilitate the entering of the first fluid, wherein the air outlet
    comprises a second recess and is in direct contact with one end of the microfluidic
    channel, the inlet is in direct contact with another end of the microfluidic channel, and the
    air outlet is not in direct contact with the inlet,
    wherein the accommodation compartment is designed in the form of a well such that the entering second fluid is retained, and a capillary valve is formed where a portion of the lower lateral side of the accommodation compartment is in communication with a portion of the lateral side of the microfluidic channel such that the first fluid and the second fluid meet each other to form an interface, and
    the inlet and the accommodation compartment are spatially separated from each other and does not directly contact each other.

2. The microfluidic multi-well-based cell culture testing device according to claim 1, wherein the wells are arranged in a 1×1, 1×2, 1×4, 2×4, 4×6, 12×8, 24×16 or 48×32 matrix.

3. The microfluidic multi-well-based cell culture testing device according to claim 1, wherein the microfluidic channel is arranged to surround the accommodation compartment such that the microfluidic well unit has a quadrangular structure.

4. The microfluidic multi-well-based cell culture testing device according to claim 1, wherein the capillary valve has a predetermined thickness and width to prevent the first fluid from entering the accommodation compartment.

5. The microfluidic multi-well-based cell culture testing device according to claim 4, wherein the thickness of the capillary valve is defined by the thickness of the microfluidic channel.

6. The microfluidic multi-well-based cell culture testing device according to claim 4, wherein the capillary valve has a thickness of 100 to 500 µm and a width of 500 µm to 2 mm.

7. The microfluidic multi-well-based cell culture testing device according to claim 1, wherein the air outlet is formed at one end of the microfluidic channel, is in communication with the upper wall of the microfluidic channel, and is exposed to the atmosphere.

8. The microfluidic multi-well-based cell culture testing device according to claim 1, wherein the first fluid is a mixture solution of a gelling agent-containing liquid medium and a biological agent, wherein the first gelling agent-containing liquid medium is immobilized; and wherein and the second fluid is a solution containing a physiologically active substance.

9. The microfluidic multi-well-based cell culture testing device according to claim 1, wherein the body of the microfluidic multi-well-based cell culture testing device is made of a transparent material.

10. The microfluidic multi-well-based cell culture testing device according to claim 1, each of the microfluidic units further comprises a bottom plate, wherein the bottom plate completely seals an entire bottom surface of the microchannel and an entire bottom surface of the accommodation compartment.

11. The microfluidic multi-well-based cell culture testing device according to claim 1, wherein the inlet is horizontally aligned with and separated from the accommodation compartment.

12. The microfluidic multi-well-based cell culture testing device according to claim 1, the accommodation compartment is located in a central region of the testing device, and the inlet is located in an outer region of the testing device.

* * * * *